United States Patent
Herak

[11] Patent Number: 5,856,475
[45] Date of Patent: Jan. 5, 1999

[54] 4-THIA-1-AZABICYCLO/3.2.0/HEPTANE-3-IMINO-2-ISOPROPYLIDENE-7-OXO-ANALOGONS OF BETA-LACTAMS, PROCESSES FOR THEIR PREPARATION AND THE USE THEREOF

[75] Inventor: Jure J. Herak, Zagreb, Croatia

[73] Assignee: Plive, farmaceutska, kemijska, prehrambena i kozmeticka industrija, dionicko drustvo, Zagreb, Croatia

[21] Appl. No.: 828,267

[22] Filed: Mar. 21, 1997

[30] Foreign Application Priority Data

Mar. 21, 1996 [HR] Croatia .................... P960131A

[51] Int. Cl.⁶ .................. C07D 499/897; C07D 499/861; C07D 499/865; C07D 499/80
[52] U.S. Cl. ........................... 540/302; 540/311
[58] Field of Search ............................. 540/302

[56] References Cited

PUBLICATIONS

Belinzoni, J. Chem Res (N), p. 1501 (1988).
Belinzoni, J Chem Res (S), p. 176 (1988).
Herak et al. Chem Abs 126, 171404 (1996).
Herak, Croatica Chem. Acta 69, 1367, 1996.

Primary Examiner—Mark L. Berch
Attorney, Agent, or Firm—Pollock, Vande Sande & Amernick

[57] ABSTRACT

The object of the present invention are 4-thia-1-azabicyclo[3.2.0]heptane-3-imino-2-isopropylidene-7-oxo beta-lactamic analogons of general formula I

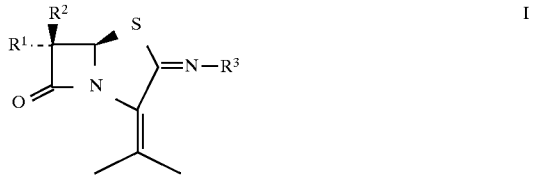

wherein the radicals have the following meanings:

$R^1$ is hydrogen or halogen,
$R^2$ is hydrogen, halogen, phthalimide,
$R^3$ is hydrogen, alkyl, benzyl, heterocycle e.g. isoxazole, pyrazole, 5-methyl-isoxazole-3-yl, 3,4-dimethyl-isoxazole-5-yl, 2-phenyl-pyrazole-3-yl, etc.

These compounds are useful as intermediates in the preparation of novel beta-lactamic analogons or of active substances in preparations for antimicrobial therapy.

13 Claims, No Drawings

4-THIA-1-AZABICYCLO/3.2.0/HEPTANE-3-IMINO-2-ISOPROPYLIDENE-7-OXO-ANALOGONS OF BETA-LACTAMS, PROCESSES FOR THEIR PREPARATION AND THE USE THEREOF

TECHNICAL FIELD OF THE INVENTION IPC
C07D 513/04

The invention relates to novel 4-thia-1-azabicyclo[3.2.0] heptane-3-imino-2-iso-propylidene-7-oxo compounds, processes for their preparation as well as to the use thereof. These compounds are novel beta-lactamic analogons of bicyclic structure comprising beta-lactam and thiazolidine ring with isopropylidene substituent in position 2 and imino substituent in position 3, and as such represent stable intermediates for further chemical transformations.

According to our findings and available prior art literature data, neither 4-thia-1-azabicyclo[3.2.0.]heptane-3-imino-2-isopropylidene-7-oxo analogons of beta-lactams nor processes for their preparation are known.

The most similar known compounds are 4-thia-1-azabicyclo[3.2.0]hept-2-ene-3-amino-7-oxo analogons of beta-lactams prepared by complex chemical transformations via azetidinone structure. In the preparation of such compounds also less stable imino penams i.e. tautomeric byproducts 4-thia-1-azabicyclo[3.2.0]heptane-3-imino-7-oxo derivatives in a yield up to 15% [Tetrahedron Lett., 28 (1987) 2283–2286] are formed.

Known are also numerous 4-thia-1-azabicyclo[3.2.0] heptane-2-isopropylidene-3,7-dioxo derivatives known as anhydropenicillins (Tetrahedron 52 (1996) 331–375], which are prepared from triethylamine salt of penicillin via mixed anhydride with trifluoracetic acid and subsequent treatment with pyridine.

The object of the present invention are novel 4-thia-1-azabicyclo[3.2.0]heptane-3-imino-2-isopropylidene-7-oxo analogons of beta-lactamic structure shown by the general formula I

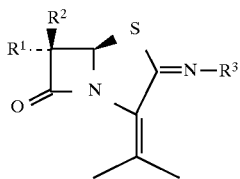

wherein the radicals have the following meanings:
$R^1$ is hydrogen or halogen,
$R^2$ is hydrogen, halogen, phthalimide,
$R^3$ is hydrogen, alkyl, benzyl, heterocycle e.g. isoxazole, pyrazole 5-methyl-isoxazole-3-yl, 3,4-dimethyl-isoxazole-5-yl, 2-phenyl-pyrazole-3-yl, etc.

A further object of the present invention is a process for the preparation of 4-thia-1-azabicyclo[3.2.0]heptane-3-imino-2-isopropylidene-7-oxo analogons of beta-lactamic structure shown by the general formula I, wherein the radicals have the above-mentioned meanings and which can be prepared by rearrangement of sulfoxides of penicillanic acid amides of the general formula II

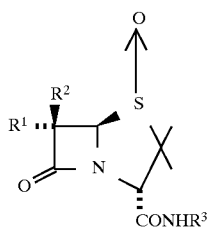

wherein the radicals have the following meanings:
$R^1$ is hydrogen or halogen,
$R^2$ is hydrogen, halogen, phthalimide,
$R^3$ is hydrogen, alkyl, benzyl, heterocycle e.g. isoxazole, pyrazole 5-methyl-isoxazole-3-yl, 3,4-dimethyl-isoxazole-5-yl, 2-phenyl-pyrazole-3-yl, etc.

The process of rearrangement of amidopenicillin of the general formula II is carried out in anhydrous inert organic solvents in the presence of phosphorous compounds at a temperature from 50° to 150° C.

Suitable inert solvents are e.g. anhydrous hydrocarbons such as benzene, toluene or xylene, ethers such as diethyl ether, dioxane or tetrahydrofurane, chlorinated hydrocarbons such as methylene chloride or chloroform, or nitrils of carboxylic acids. Suitable phosphorous compounds are trimethyl phosphite, triethyl phosphite, triphenyl phosphine and other phosphorous compounds of lower oxidation level.

The preparation of suitable starting compounds of the general formula II was the object of our previous invention described in Croatian patent application No. P 940345A of Oct. 6, 1994 entitled "Novel Derivatives of 2-Oxoazetidine, Methods for Preparation, Intermediates, Salts and Use" or is described in the literature [J. Chem. Research (S), 176; (M) 1501 (1988)].

Their proclivity to rearrangement into novel bicyclic beta-lactamic analogons of the general formula I was found during the investigation of Cooper's rearrangement of sulfoxides of penicillanic acid not possessing an amide side chain in position 6. The original Cooper's rearrangement [J. Am. Chem. Soc. 92, 2575 (1972]; Rearrangements of Cephalosporins and Penicillins in Cephlalosporins and Penicillins;. eds. E. H. Flynn, Academic Press, New York, 1972, p. 201] is a well-known process for the preparation of thiazoline-azetidine bicyclic structure by reductive rearrangement starting from penicillin G sulfoxide. Such rearrangement necessitates the use of protected carboxy acid such as esters and free carboxamide chain in position 6 as found in penicillins G and V.

Now it has been found that starting from sulfoxides of penicillanic acid of the general formula II i.e. from compounds of the penam structure having an amide group in position 2 but not possessing an amide side chain in position 6, in conditions similar to those of Cooper's rearrangement, there are formed compounds of penicillanic structure I with an isopropylidene substituent in position 2 and an imino substituent in position 3.

A special case is the rearrangement of sulfoxides of penicillanic acid amides of the general formula II, wherein the radicals have the following meanings:
$R^1$ is halogen,
$R^2$ is halogen,
$R^3$ is hydrogen, alkyl, benzyl, heterocycle e.g. isoxazole, pyrazole 5-methyl-isoxazole-3-yl, 3,4-dimethyl-isoxazole-5-yl, 2-phenyl-pyrazole-3-yl, etc.,
whereat before and during the rearrangement there may occur hydrodehalogenation and the formation of penicillanic acid amides of the general formula II, wherein the radicals have the following meanings:

$R^1$ is hydrogen, halogen, $R^2$ is hydrogen, halogen, $R^3$ is hydrogen, alkyl, benzyl, heterocycle e.g. isoxazole, pyrazole 5-methyl-isoxazole-3-yl, 3,4-dimethyl-isoxazole-5-yl, 2-phenyl-pyrazole-3-yl, etc., whereat these compounds may be either isolated or without isolation further rearranged into the beta-lactamic structure shown by the general formula I, wherein the radicals have the following meanings:

$R^1$ is hydrogen, halogen, $R^2$ is hydrogen, halogen, $R^3$ is hydrogen, alkyl, benzyl, heterocycle e.g. isoxazole, pyrazole 5-methyl-isoxazole-3-yl, 3,4-dimethyl-isoxazole-5-yl, 2-phenyl-pyrazole-3-yl, etc.

All reactions are carried out under usual reaction conditions and the formed products are isolated upon the treatment of the reaction mixture by crystallization or chromatography on a silica gel column.

A further object of the invention relates to the use of these compounds as useful reactants in a process for the preparation of novel monocyclic beta-lactams, potential intermediates for the preparation of beta-lactamic antibiotics or synergists of beta-lactamic antibiotics from the class of penems, oxipenems and carbapenems as well as to other possibilities offered by these substrates.

A further object of the present invention relates to the use of these compounds as active components in ready-to-use medicaments with synergistic action in combination with other beta-lactamic antibiotics such as ampicillin.

The present invention is illustrated by the following non-limiting examples.

(2S,4R,5R,6S)-2-Benzyl-carbamoyl-6-bromo-3,3-dimethyl-7-oxo-4-thia-1-azabicyclo-[3.2.0]heptane-4-oxide

EXAMPLE 1

A suspension of (2S,4R,5R)-2-benzyl-carbamoyl-6,6-dibromo-3,3-dimethyl-7-oxo-4-thia-1-azabicyclo[3.2.0]heptane-4-oxide (1160 mg, 2.5 mmole) and triethylphosphite (837 mg, 5 mmole) in dry benzene (30 ml) was stirred at room temperature for 3 hours, whereby a clear solution was formed. The reaction mixture was treated with water and the layers were separated. The organic layer was washed with water, then with a saturated sodium hydrogen carbonate solution and again with water. The evaporation of dried ($Na_2SO_4$) organic layer under reduced pressure gave an oily residue, which upon chromatography on silica gel resulted in (2S,4R,5R,6S)-2-benzyl-carbamoyl-6-bromo-3,3-dimethyl-7-oxo-4-thia-1-azabicyclo[3.2.0]heptane-4-oxide (810 mg, 84.2%). Crystallization from diethyl ether gave the product in the form of a white crude solid.

M.p. 134°–135° C.

$R_f$ 0.40 [methylen chloride: ethyl acetate (2:1, v/v)].

$[\alpha]^{20}_D$=+179° (c 1, $CH_2Cl_2$).

IR (KBr) $\nu_{max}$/cm$^{-1}$: 3295s, 2980m, 1790vs, 1655s, 1530m, 1280m, 1240m, 1050s.

$^1$H NMR (300 MHz, $CDCl_3$) δ: 1.39 and 1.67 (each 3H, s, $CMe_2$), 4.34 (1H, s, 3-H), 4.40 and 4.50 (each 1H, dd, J 5.5, 6.4 and 14.6, $CH_2$), 4.64 (1H, d, J 1.5, 6-H), 5.14 (1H, d, J 1.5, 5-H), 6.90 (1H, br, NH), 7.27–7.40 (5H, m, $C_6H_5$).

Anal. for $C_{15}H_{17}BrN_2O_3S$ Found.: C 46.45; H 4.50; N 7.15; S 8.10%. Calc.: C 46.76; H 4.45; N 7.27; S 8.32%.

EXAMPLE 2

(2S,4R,5R,6S)-2-Benzyl-carbamoyl-6-bromo-3,3-dimethyl-7-oxo-4-thia-1-azabicyclo-[3.2.0]heptane-4-oxide was obtained by stirring (2S,4R,5R)-2-benzyl-carbamoyl-6,6-dibromo-3,3-dimethyl-7-oxo-4-thia-1-azabicyclo[3.2.0]heptane-4-oxide and triethyl phosphite in cold (0° C.) methylene chloride for 30 minutes. After the completed reaction the reaction mixture was treated as in Example 1 and recrystallized from diethyl ether.

(2S,4S,5R,6S)-2-Benzyl-carbamoyl-6-bromo-3,3-dimethyl-7-oxo-4-thia-1-azabicyclo[-3.2.0]heptane-4-oxide

EXAMPLE 3

To a cold (0° C.) solution of (2S,4R,5R)-2-benzyl-carbamoyl-6,6-dibromo-3,3-dimethyl-7-oxo-4-thia-1-azabicyclo[3.2.0]heptane-4-oxide (1160 mg, 2.5 mmole) in dry methylene chloride (30 ml) triphenyl phosphine (837 mg, 5 mmole) was added and it was stirred for 15 minutes. The reaction mixture was treated with water and the layers were separated. The organic layer was washed with water, then with a saturated sodium hydrogen carbonate solution and again with water. The evaporation of dry ($Na_2SO_4$) organic layer under reduced pressure gave a foamy residue, which after chromatography on silica gel gave (2S,4S,5R,6S)-2-benzyl-carbamoyl-6-bromo-3,3-dimethyl-7-oxo-4-thia-1-azabicyclo[3.2.0]heptane-4-oxide (780 mg, 81.0%). Crystallization from diethyl ether gave the product as a white crystalline powder.

M.p. 141°–143° C.

$R_f$ 0.45 [methylene chloride : ethyl acetate (2:1, v/v)].

$[\alpha]^{20}_D$=+213° (c 1, $CH_2Cl_2$).

IR (KBr) $\nu_{max}$/cm$^{-1}$: 3335m, 2980m, 1795vs, 1660s, 1525m, 1275m, 1040m.

$^1$H NMR (300 MHz, $CDCl_3$) δ: 1.24 and 1.78 (each 3H, s, $CMe_2$), 4.47 (1H, s, 3-H), 4.37 and 4.57 (each 1H, dd, J 6.0, 6.3 and 14.7, $CH_2$), 4.97 (1H, d, J 1.5, 6-H), 5.12 (1H, d, J 1.5, 5-H), 6.90 (1H, br, NH), 7.23–7.38 (5H, m, $C_6H_5$).

Anal. for $C_{15}H_{17}BrN_2O_3S$ Found.: C 46.55; H 4.32; N 7.50; S 8.15%. Calc.: C 46.76; H 4.45; N 7.27; S 8.32%.

EXAMPLE 4

(2S,4S,5R,6S)-2-Benzyl-carbamoyl-6-bromo-3,3-dimethyl-7-oxo-4-thia-1-azabicyclo[-3.2.0]heptane-4-oxide was obtained by heating (2S,4R,5R)-2-benzyl-carbamoyl-6,6-dibromo-3,3-dimethyl-7-oxo-4-thia-1-azabicyclo[3.2.0]heptane-4-oxide and triphenyl phosphine in toluene at 50° C. for 15 minutes. After completed reaction the reaction mixture was treated as in Example 3 and recrystallized from diethyl ether.

(5R,6S)-3-Benzylimino-6-bromo-2-isopropylidene-7-oxo-4-thia-1-azabicyclo[3.2.0]-heptane.

EXAMPLE 5

A suspension of (2S,4R,5R,6S)-2-benzyl-carbamoyl-6-bromo-3,3-dimethyl-7-oxo-4-thia-1-azabicyclo[3.2.0]heptane-4-oxide (200 mg, 0.52 mmole) and triethyl phosphite (863 mg, 5.2 mmole) in dry benzene (30 ml) was stirred under reflux for 13 hours. The cooled reaction mixture was rinsed with water (20 ml), 1N hydrochloric acid and again with water. The organic extract was dried over sodium sulphate, filtered and evaporated to dryness in vacuum and the oily residue, upon chromatography on silica gel, gave (5R,6S)-3-benzylimino-6-bromo-2-isopropylidene-7-oxo-4-thia-1-azabicyclo [3.2.0]heptane (129 mg, 70.7%). Recrystallization from a mixture of diethyl ether and n-hexane gave a white crude product.

M.p. 64°–66° C.

$R_f$ 0.55 (toluene).

$[\pi]^{t0}_D$=+84.60 (c 1, $CH_2Cl_2$).

MS m/z M+ 351.

IR (film) $v_{max}$./cm$^{-1}$: 2990w, 2910w, 1790vs, 1630vs, 1450w, 1350m, 1300s, 1160m, 1090m, 1030m.

$^1$H NMR (300 MHz, CDCl$_3$) δ: 2.12 and 2.30 (each 3H, s, CMe$_2$), 4.50 and 4.57 (each 1H, d, J 16.4 =NCH$_2$), 4.92 (1H, d, J 0.9, 6-H), 5.29 (1H, d, J 0.9, 5-H), 7.25–7.36 (5H, m, C$_6$H$_5$).

Anal. for C$_{15}$H$_{15}$BrN$_2$OS Found.: C 51.29; H 4.35; N 7.58%. Calc.: C 49.67; H 4.22; N 7.25%.

EXAMPLE 6

(5R,6S)-3-Benzylimino-6-bromo-2-isopropylidene-7-oxo-4-thia-1-azabicyclo[3.2.0] heptane was obtained by heating (2S,4S,5R,6S)-2-benzyl-carbamoyl-6-bromo-3,3-dimethyl-7-oxo-4-thia-1-azabicyclo[3.2.0]heptane-4-oxide and triphenyl phosphine in hot toluene for 10 hours. After completed reaction the reaction mixture was treated as in Example 5 and recrystallized from a mixture of diethylether and n-hexane.

EXAMPLE 7

(5R,6S)-3-Benzylimino-6-bromo-2-isopropylidene-7-oxo-4-thia-1-azabicyclo[3.2.0] heptane was obtained by heating (2S,4R,5R)-2-benzyl-carbamoyl-6,6-dibromo-3,3-dimethyl-7-oxo-4-thia-1-azabicyclo[3.2.0]heptane-4-oxide and triethyl phosphite in hot toluene for 10 hours. After completed reaction the reaction mixture was treated as in Example 5 and recrystallized from a mixture of diethyl ether and n-hexane.

(5R)-3-Benzylimino-2-isopropylidene-7-oxo-4-thia-1-azabicyclo[3.2.0] heptane

EXAMPLE 8

A suspension of (2S,4R,5R)-2-benzyl-carbamoyl-3,3-dimethyl-7-oxo-4-thia-1-aza-bicyclo[3.2.0]heptane-4-oxide (306 mg, 1.0 mmole), triethyl phosphite (863 mg, 5.2 mmole) in dry benzene (30 ml) was stirred under reflux for 30 hours. The cooled reaction mixture was rinsed with water (20 ml), 1N hydrochloric acid and again with water. The organic extract was dried over sodium sulphate, filtered and evaporated in the vacuum of a water suction pump to a dry residue giving, after chromatography on a silica gel column, (5R)-3-benzylimino-2-isopropylidene-7-oxo-4-thia-1-azabicyclo-[3.2.0] heptane as a white crystalline powder. M.p. 73°–74° C. (diethyl ether).
R$_f$ 0.28 (toluene).
[α]$^{20}_D$=+233.2° (c 1, CH$_2$Cl$_2$).
MS m/z M+ 272.

IR (film) $v_{max}$./cm$^{-1}$: 2960w, 2910w, 1780vs, 1630vs, 1450w, 1410m, 1350s, 1300vs, 1250m, 1220m, 1200m, 1150w, 1100m, 1010m.

$^1$H NMR (300 MHz, CDCl$_3$) δ: 2.09 and 2.30 (each 3H, S, CMe$_2$), 3.27 (1H, d, J 1.7, 6β-H), 3.73 (1H, d, J 4.1, 6α-H) 4.51 and 4.57 (each 1H, d, J 16.8 =NCH$_2$), 5.19 (1H, dd, J 1.7 and 4.1, 5-H), 7.23–7.38 (5H, m, C$_6$H$_5$).

Anal. for C$_{15}$H$_{16}$N$_2$OS Found.: C 66.07; H 5.92; N 10.26%. Calc.: C 66.14; H 6.05; N, 10.29%.

EXAMPLE 9

(5R)-3-Benzylimino-2-isopropylidene-7-oxo-4-thia-1-azabicyclo[3.2.0] heptane was also obtained by stirring a suspension of (5R,6S)-3-benzylimino-6-bromo-2-isopropylidene-7-oxo-4-thia-1-azabicyclo[3.2.0]heptane (200 mg, 0.57 mmole), NaHCO$_3$ (5% water solution, 15 ml) and 10% Pd-C catalyst (200 mg) in ethyl acetate (20 ml) at room temperature for 2 hours under the pressure of 2 atm. The suspension was filtered through Celite and the layers were separated. The organic layer was washed with brine, dried (Na$_2$SO$_4$) and evaporated under the reduced pressure of a water suction pump and the residue was treated as described in Example 8.

I claim:
1. 4-Thia-1-azabicyclo[3.2.0]heptane-3-imino-2-isopropylidene-7 oxo analogons of beta-lactams of the formula I

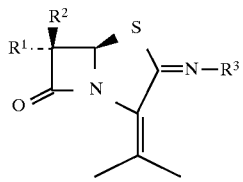

wherein the radicals have the following meanings:
R$_1$ is hydrogen or halogen,
R$_2$ is hydrogen, halogen or phthalimide,
R$_3$ is hydrogen, alkyl, benzyl, isoxazole, pyrazole, 5-methyl-isoxazole-3-yl, 3,4 dimethyl-isoxazole-5-yl, or 2-phenyl-pyrazole-3-yl.
2. A compound according to claim 1, characterized in that R$^1$ is hydrogen, R$^2$ is hydrogen and R$^3$ is PhCH$_2$.
3. A compound according to claim 1, characterized in that R$^1$ is bromine, R$^2$ is hydrogen and R$^3$ is PhCH$_2$.
4. A compound according to claim 1, characterized in that R$^1$ is bromine, R$^2$ is hydrogen and R$^3$ is methyl.
5. A compound according to claim 1, characterized in that R$^1$ is bromine, R$^2$ is hydrogen and R$^3$ is 5-methyl-isoxazole-3-yl.
6. A compound according to claim 1, characterized in that R$^1$ is bromine, R$^2$ is hydrogen and R$^3$ is 3,4-dimethyl-isoxazole-5-yl.
7. A compound according to claim 1, characterized in that R$^1$ is bromine, R$^2$ is hydrogen and R$^3$ is 2-phenyl-pyrazole-3-yl.
8. A compound according to claim 1, characterized in that R$^1$ is bromine, R$^2$ is hydrogen and R$^3$ is hydrogen.
9. A compound according to claim 1, characterized in that R$^1$ is bromine, R$^2$ is bromine and R$^3$ is PhCH$_2$.
10. A compound according to claim 1, characterized in that R$^1$ is chlorine, R$^2$ is hydrogen and R$^3$ is PhCH$_2$.
11. A compound according to claim 1, characterized in that R$^1$ is chlorine, R$^2$ is chlorine and R$^3$ is PhCH$_2$.
12. A compound according to claim 1, characterized in that R$^1$ is hydrogen, R$^2$ is phtalimide and R$^3$ is PhCH$_2$.
13. A process for the preparation of 4-thia-1-azabicyclo [3.2.0]heptane-3-imino-2-isopropylidene-7-oxo analogons of beta-lactams of the formula I, wherein the radicals have the meanings given in claim 1, characterized in that sulfoxides of penicillanic acid amides of the formula II

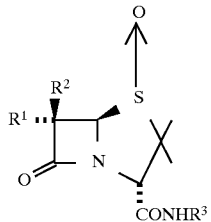

wherein the radicals have the following meanings:
R$^1$ is hydrogen or halogen
R$^2$ is hydrogen, halogen or phthalimide, R³ is hydrogen, alkyl, benzyl, isoxazole, pyrazole, 5-methyl-isoxazole-3-yl, 3,4-dimethyl-isoxazole-5-yl, or 2-phenyl-pyrazole-3-yl,
are subjected to a reaction with trimethyl phosphite, triethyl phosphite, or triphenyl phosphine in a dry organic aprotic solvent at 50° to 150° C. and the reaction mixture is treated with water and a product is isolated by crystallization or by chromatography on a silica gel column.

* * * * *

UNITED STATES PATENT AND TRADEMARK OFFICE
CERTIFICATE OF CORRECTION

PATENT NO. : 5,856,475
DATED : January 5, 1999
INVENTOR(S) : Herak

It is certified that error appears in the above-identified patent and that said Letters Patent is hereby corrected as shown below:

Title page, Item [73] Assignee should read:

"Pliva , farmaceutska, kemijska, prehrambena i kozmeticka industrija, dionicko drustvo".

Signed and Sealed this

Eleventh Day of May, 1999

*Attest:*

Q. TODD DICKINSON

*Attesting Officer*      Acting Commissioner of Patents and Trademarks